(12) United States Patent
Fowler et al.

(10) Patent No.: US 7,211,091 B2
(45) Date of Patent: May 1, 2007

(54) FINGERTIP-ACTUATED SURGICAL CLIP APPLIER AND RELATED METHODS

(75) Inventors: David N. Fowler, Raleigh, NC (US); James D. Segermark, Gem Lake, MN (US); Christopher J. Herman, White Bear Lake, MN (US)

(73) Assignee: Pilling Weck Incorporated, Limerick, PA (US)

( * ) Notice: Subject to any disclaimer, the term of this patent is extended or adjusted under 35 U.S.C. 154(b) by 507 days.

(21) Appl. No.: 10/229,168

(22) Filed: Aug. 27, 2002

(65) Prior Publication Data

US 2004/0044352 A1   Mar. 4, 2004

(51) Int. Cl.
*A61B 17/10* (2006.01)
*A61B 17/122* (2006.01)
*A61B 17/00* (2006.01)

(52) U.S. Cl. .................... 606/142; 606/205
(58) Field of Classification Search ............ None
See application file for complete search history.

(56) References Cited

U.S. PATENT DOCUMENTS

| | | | |
|---|---|---|---|
| 2,412,255 A * | 12/1946 | Ferguson | 294/99.2 |
| 2,517,168 A * | 8/1950 | Bennek | 452/117 |
| 3,270,745 A | 9/1966 | Wood | |
| 3,326,216 A | 6/1967 | Wood | |
| 3,439,522 A | 4/1969 | Wood | |
| 3,439,523 A | 4/1969 | Wood | |
| 4,146,130 A | 3/1979 | Samuels et al. | |
| 4,375,866 A | 3/1983 | Giersch et al. | |
| 4,509,518 A | 4/1985 | McGarry et al. | |
| 4,646,740 A | 3/1987 | Peters et al. | |
| 4,662,555 A | 5/1987 | Thornton | |
| 4,834,096 A | 5/1989 | Oh et al. | |
| 5,038,991 A | 8/1991 | Thornton | |
| 5,047,038 A | 9/1991 | Peters et al. | 606/139 |
| 5,062,846 A | 11/1991 | Oh et al. | 606/158 |
| 5,100,416 A | 3/1992 | Oh et al. | 606/139 |
| 5,104,397 A * | 4/1992 | Vasconcelos et al. | 606/206 |
| 5,112,343 A | 5/1992 | Thornton | 606/143 |
| 5,135,530 A * | 8/1992 | Lehmer | 606/107 |
| 5,403,327 A | 4/1995 | Thornton et al. | 606/143 |
| 5,509,920 A | 4/1996 | Phillips et al. | 606/157 |
| 5,527,320 A | 6/1996 | Carruthers et al. | 606/143 |
| 5,634,930 A | 6/1997 | Thornton et al. | 606/143 |
| 5,674,228 A * | 10/1997 | Henderson et al. | 606/137 |
| 5,833,698 A | 11/1998 | Hinchliffe et al. | 606/153 |
| 5,868,761 A | 2/1999 | Nicholas et al. | 606/143 |

(Continued)

*Primary Examiner*—Glenn K. Dawson
(74) *Attorney, Agent, or Firm*—Baker & Hostetler LLP

(57) ABSTRACT

A fingertip-actuated surgical clip applier includes a first body and a second body substantially structurally identical to the first body. The first body includes a main section and a first jaw extending in a distal direction from the main section. The main section includes a hinge region and a first longitudinal wall extending between the first jaw and the hinge region. The first longitudinal wall includes a first outside surface adapted for contacting a first fingertip. The second body includes a second jaw and a second longitudinal wall. The second longitudinal wall includes a second outside surface adapted for contacting a second fingertip. The second body is inverted in relation to the first body and is pivotably connected to the hinge region. The first and second jaws are pivotable toward each other to a closed position and away from each other to an open position.

8 Claims, 10 Drawing Sheets

U.S. PATENT DOCUMENTS

| | | | |
|---|---|---|---|
| 5,925,064 A | * 7/1999 | Meyers et al. | 606/205 |
| 5,951,574 A | 9/1999 | Stefanchik et al. | 606/143 |
| 6,000,941 A | * 12/1999 | Ingels | 433/159 |
| 6,391,035 B1 | * 5/2002 | Appleby et al. | 606/142 |

* cited by examiner

FINGERTIP-ACTUATED SURGICAL CLIP APPLIER AND RELATED METHODS

TECHNICAL FIELD

The present invention generally relates to surgical clip applying instruments and their use in manipulating clips in surgical procedures such as vessel ligation. More particularly, the present invention relates to a fingertip-actuated clip applier capable of compressing asymmetric clips by using a pair of fingertips such as the tips of the index finger and thumb.

BACKGROUND ART

Many surgical procedures require vessels or other tissues of the human body to be ligated during the surgical process. For example, many surgical procedures require cutting blood vessels (e.g., veins or arteries), and these blood vessels may require ligation to reduce bleeding. In some instances, a surgeon may wish to ligate the vessel temporarily to reduce blood flow to the surgical site during the surgical procedure. In other instances a surgeon may wish to permanently ligate a vessel. Ligation of vessels or other tissues can be performed by closing the vessel with a ligating clip, or by suturing the vessel with surgical thread. The use of surgical thread for ligation requires complex manipulations of the needle and suture material to form the knots required to secure the vessel. Such complex manipulations are time-consuming and difficult to perform, particularly in endoscopic surgical procedures that afford limited space and visibility. By contrast, ligating clips are relatively easy and quick to apply. Accordingly, the use of ligating clips in both endoscopic and open surgical procedures has grown dramatically.

Various types of hemostatic and aneurysm clips are used in surgery for ligating blood vessels or other tissues to stop the flow of blood. Such clips have also been used for interrupting or occluding ducts and vessels in particular surgeries such as sterilization procedures. Typically, a clip is applied to the vessel or other tissue by using a dedicated mechanical instrument commonly referred to as a surgical clip applier, ligating clip applier, or hemostatic clip applier. A clip applier designed for use with asymmetric plastic clips in an open (i.e., non-endoscopic) surgical procedure is disclosed in U.S. Pat. No. 5,100,416 to Oh et al., assigned to the assignee of the present invention. The clip applier is used to position the clip over the desired vessel and its jaws are actuated, typically using an actuating mechanism disposed in the handle of the device, to close the clip about the vessel. The clip is typically left in place after application to the tissue until hemostasis or occlusion occurs. At some point thereafter, the clip is removed by using a separate instrument dedicated for that purpose, i.e., a clip removal instrument. A clip remover designed for use with asymmetric plastic clips in open surgery is disclosed in U.S. Pat. No. 6,391,035 to Appleby et al., assigned to the assignee of the present invention.

Ligating clips can be classified according to their geometric configuration (e.g., symmetric clips or asymmetric clips), and according to the material from which they are manufactured (e.g., metal clips or polymeric clips). Symmetric clips are generally "U" or "V" shaped and thus are substantially symmetrical about a central, longitudinal axis extending between the legs of the clip. Symmetric clips are usually constructed from metals such as stainless steel, titanium, tantalum, or alloys thereof. By means of a dedicated clip applier, the metal clip is permanently deformed over the vessel. An example of one such clip is disclosed in U.S. Pat. No. 5,509,920 to Phillips et al. An example of a metallic clip applier is disclosed in U.S. Pat. No. 3,326,216 to Wood, in which a forceps-type applier having conformal jaws is used to grip and maintain alignment of the clip during deformation. Such appliers may additionally dispense a plurality of clips for sequential application, as disclosed in U.S. Pat. No. 4,509,518 to McGarry et al.

With the advent of high technology diagnostic techniques using computer tomography (CATSCAN) and magnetic resonance imaging (MRI), metallic clips have been found to interfere with the imaging techniques. To overcome such interference limitations, biocompatible polymers have been increasingly used for surgical clips. Unlike metallic clips, which are usually symmetric, polymeric clips are usually asymmetric in design and hence lack an axis of symmetry. Inasmuch as the plastic clip cannot be permanently deformed for secure closure around a vessel or other tissue, latching mechanisms have been incorporated into the clip design to establish closure conditions and to secure against re-opening of the vessel. For example, polymeric clips are disclosed in U.S. Pat. No. 4,834,096 to Oh et al. and U.S. Pat. No. 5,062,846 to Oh et al., both of which are assigned to the assignee of the present invention. These plastic clips generally comprise a pair of curved legs joined at their proximal ends with an integral hinge or heel. The distal ends of the curved legs include interlocking latching members. The distal end of one leg terminates in a lip or hook structure into which the distal end of the other leg securely fits to lock the clip in place. The distal ends of the clips taught by Oh et al. also include lateral bosses that are engaged by the jaws of the clip applier.

A clip applier specifically designed for asymmetric plastic clips, such as the aforementioned U.S. Pat. No. 5,100,416 to Oh et al., is used to close the clip around the tissue to be ligated, and to latch or lock the clip in the closed condition. In operation, the jaws of this clip applier are actuated into compressing contact with the legs of the clip. This causes the legs to pivot inwardly about the hinge, thereby deflecting the hook of the one leg to allow reception therein of the distal end of the other leg.

In addition to compatibility with sophisticated diagnostic techniques, asymmetric clips have other advantages over symmetric clips. For example, because asymmetric clips are formed from polymeric materials, the mouths of asymmetric clips can be opened wider than the mouths of symmetric clips. This allows a surgeon to position the clip about the desired vessel with greater accuracy. In addition, a clip of the type described in U.S. Pat. Nos. 4,834,096 and 5,062,846 can be repositioned before locking the clip on the vessel or before removing the clip from the vessel, in a process referred to as "approximating" the clip.

As indicated above, U.S. Pat. No. 5,100,416 to Oh et al. discloses a clip applier designed for use with asymmetric plastic clips in an open (i.e., non-endoscopic) surgical procedure. Other types of clip appliers have been developed for applying metallic clips. Clip appliers can also be classified according to whether they are designed for either open or endoscopic surgical procedures. Clip appliers designed for use with metallic clips in open surgery are disclosed in U.S. Pat. No. 3,270,745 to Wood; U.S. Pat. No. 3,326,216 to Wood; U.S. Pat. No. 3,439,522 to Wood; U.S. Pat. No. 3,439,523 to Wood; U.S. Pat. No. 4,146,130 to Samuels et al.; U.S. Pat. No. 4,646,740 to Peters et al. (assigned to the assignee of the present invention); U.S. Pat. No. 4,509,518 to McGarry et al.; U.S. Pat. No. 5,047,038 to Peters et al.

(assigned to the assignee of the present invention); and U.S. Pat. No. 5,104,395 to Thornton et al. (assigned to the assignee of the present invention). Clip appliers designed for use with metallic clips in endoscopic surgery are disclosed in U.S. Pat. No. U.S. Pat. No. 5,403,327 to Thornton et al.; U.S. Pat. No. 5,112,343 to Thornton; U.S. Pat. No. 5,527,320 to Carruthers et al.; and U.S. Pat. No. 5,634,930 to Thornton et al., all of which are assigned to the assignee of the present invention.

As a general matter, endoscopic, and other minimally invasive surgical techniques enable surgeons to perform complex procedures through relatively small entry points, or surgical ports, in the body. Endoscopic surgery involves the use of an endoscope, which is an instrument permitting the visual inspection and magnification of a body cavity. The endoscope is inserted into a body cavity through a cannula extending through a hole or port in the soft tissue protecting the body cavity. The port is typically made with a trocar, which includes a cutting instrument slidably and removably disposed within a trocar cannula. After forming the port, the cutting instrument can be withdrawn from the trocar cannula. A surgeon can then perform diagnostic and/or therapeutic procedures at the surgical site with the aid of specialized medical instruments adapted to fit through the trocar cannula and additional trocar cannulas providing openings into the desired body cavity. Minimally invasive surgical techniques are often desirable due to reduced trauma to the patient, reduced likelihood of infection at the surgical site, and lower overall medical costs.

Laparoscopic techniques are another type of minimally invasive procedure. The term "laparoscopic" refers to surgical procedures performed on the interior of the abdomen. One common laparoscopic procedure is hand-assisted laparoscopic surgery or HALS. In a typical HALS procedure, the surgeon uses a scalpel to make an abdominal incision. This incision is large enough to allow sufficient access of the surgeon's hand and forearm to the desired operative area in the abdomen. An inflatable device that includes two resilient rings attached to a translucent, polymeric cuff or sleeve is then inserted through the incision. The device is manipulated so as to form a port circumscribed by the incision, with one of the rings contacting the outer surface of the abdominal wall and the other ring contacting the inner surface of the abdominal wall. The surgeon then inserts one hand and forearm through the incisional area shaped by the port and into the peritoneal cavity of the abdomen, with the translucent sleeve surrounding the hand and forearm. The surgeon then uses his other hand to operate a manual inflation pump that is fluidly connecting to the sleeve through surgical-grade tubing. The device is consequently inflated so as to effect a seal between the surgeon's inserted forearm and the abdominal incision. The abdomen is then insufflated with a gas while the surgeon's hand remains in the peritoneal cavity, allowing the surgeon to move this hand around while using his other hand to manipulate one or more endoscopic devices, such as a clip applier, through a separately located trocar cannula.

Clip appliers can be further classified according to whether they are manual or automatic. The term "automatic" denotes the kind of clip appliers that retain a plurality of hemostatic clips adjacent to the jaws of a clip applier in a way such that a new clip is automatically fed to the jaws after the previous clip has been crimped or latched into place. Automatic clip appliers are disclosed in the aforementioned U.S. Pat. Nos. 4,509,518; 4,646,740; 5,047,038; 5,104,395; 5,112,343; 5,403,327; 5,527,320; and 5,634,930.

By contrast, the term "manual" denotes the kind of clip appliers that receive one clip at a time between the jaws, and which have to be reloaded manually after the previous clip has been crimped or latched. These manual instruments usually have a forceps-type design. The reloading operation is generally accomplished by inserting the jaws of the applier into a clip holder or cartridge and engaging or grasping a clip contained therein. Many types of clip cartridges currently available contain a plurality of longitudinally-spaced clip-retaining chambers. A single clip is retained in each chamber by a variety of means, and is removed from its chamber by a forceps-type clip applier that is inserted into the selected clip chamber and secured to the clip sufficiently to overcome whatever clip retention means is utilized, thereby enabling the clip to be removed from the clip chamber. Manual clip appliers are disclosed in the aforementioned U.S. Pat. Nos. 3,270,745; 3,326,216; 3,439,522; 3,439,523; 4,146,130; and 5,100,416.

Conventional clip appliers of all types discussed above include a pair of jaws, and a handle or grip assembly designed for manipulation by the hand and fingers of the user to actuate the jaws. In addition, an elongate (e.g., 11 inches) intermediate section separates the jaws and the handle assembly. This intermediate section is usually a shaft section in the case of automatic and/or endoscopic clip appliers, or a pair of pivoting arms in the case of most manual clip appliers. In the case of a shaft section, some type of linkage is provided in the shaft section and/or the handles through which the force imparted by the surgeon's hand to move the handles (e.g., squeezing) is transferred into pivoting of the jaws and thus compression of the clip.

It is thus evident that for conventionally designed clip appliers, the surgeon's hand is remotely located with respect to the jaws and the clip loaded into the jaws, due to the intervening shaft assembly. Moreover, the shaft assembly or pair of forceps-style arms are designed to provide mechanical assistance and leverage when using the handles to actuate the jaws. While such conventional features in most cases serve the intended purposes of the clip applier well, it is acknowledged that the degree of "feel" of the clip in the jaws afforded to the surgeon is not optimal. It is further acknowledged that the lengthy configuration of conventional clip appliers is not always needed, especially in HALS procedures and non-endoscopic procedures where large-area access is already provided to the surgical site. In addition, the mechanical assistance provided by the conventional configuration is not always needed. This is especially true with respect to polymeric clips, which do not require much force to compress in comparison to metallic clips.

Therefore, many types of surgical procedures could be facilitated by providing a clip applier having a much smaller configuration than has heretofore been available. Applicant has discovered an improved fingertip clip applier that meets the long-felt need for such a device.

DISCLOSURE OF THE INVENTION

In general terms, the present invention provides a clip applying instrument that is advantageously employed to manipulate surgical clips such as ligating clips, and especially polymeric, latchable clips of asymmetric design such as those described herein by way of example. The present invention takes into account the fact that polymeric clips require much less force to be deflected, compressed or otherwise manipulated during the course of a surgical procedure as compared with metallic clips. Accordingly, for many surgical procedures, the mechanical assistance and leverage provided by previously available clip appliers of conventional forceps-type or shaft/linkage design, which have large-dimensioned features such as shafts or arms and/or force-transmitting/multiplying components, is not needed. The low forces required to latch a polymeric clip enable the clip applier of the present invention to have a significantly smaller size in comparison to conventional clip appliers, and enable the clip applier to be actuated sufficiently by forces imparted by the fingertips of the surgeon or user. Thus, the clip applier of the present invention has a relatively simple structure. The clip applier generally comprises a pair of opposing jaws for handling a surgical clip, and a pair of opposing areas that are contacted by opposing fingertips of the user such as the tips of the index finger and the thumb. Once a clip has been loaded into the jaws, the jaws can be compressed by squeezing the fingertips together by application of low forces imparted by the user.

During operation of the clip applier of the present invention, the fingertips of the user are very close to the jaws of the clip applier and thus close to the clip being manipulated. This configuration provides the user with a high level of tactile feedback or "feel", and consequently improved control over the clip and the procedure being performed. The design of the clip applier of the present invention and its small size not only afford the user precise control over placement of the clip, but also allows greater maneuverability of the clip within or at the surgical site. The compact size also allows the clip applier to be employed at surgical sites where conventional larger clip appliers cannot fit.

In addition to the miniature size of the clip applier of the present invention, the clip applier was designed so as to be assembled from two identical or substantially identical body pieces or halves. That is, a first body piece is manufactured, a similar or identical second body piece is manufactured, and the two body pieces are then assembled by snapping them together to form the clip applier of the present invention. As will become evident from the detailed description below, these two body pieces contain all the features necessary for the successful operation of the clip applier. Preferably, the cost of the clip applier is minimized and its manufacturing simplified further by constructing the body pieces from an appropriate polymeric material. The low cost of the resulting clip applier justifies its use as a single-use instrument that can be disposed of after one surgical procedure if desired, thereby eliminating the requirement for post-procedure sterilization of the clip applying instrument.

According to one embodiment of the present invention, a fingertip-actuated surgical clip applier comprises a first body and a second body substantially structurally identical to the first body. The first body comprises a main section and a first jaw extending in a distal direction from the main section. The main section comprises a hinge region and a first longitudinal wall extending between the first jaw and the hinge region. The first longitudinal wall comprises a first outside surface adapted for contacting a first fingertip. The second body comprises a second jaw and a second longitudinal wall. The second longitudinal wall comprises a second outside surface adapted for contacting a second fingertip. The second body is inverted in relation to the first body and is pivotably connected to the hinge region. The first and second jaws are pivotable toward each other to a closed position and away from each other to an open position.

Preferably, each body of the clip applier has a unitary, polymeric construction.

Preferably, the clip applier, when at the closed position, has a gap defined between the first and second jaws to prevent the first and second jaws from contacting each other.

Preferably, the first and second outside surfaces of the clip applier comprises contoured areas for contact with the first and second fingertips, respectively.

According to another embodiment of the present invention, the first body comprises a first boss and a first aperture, and the second body comprises a second boss and a second aperture. The first boss is pivotably disposed within the second aperture, and the second boss is pivotably disposed within the first aperture. A first rib extends from the first body toward the second body, and a second rib extends from the second body toward the first body. At both the open and closed positions of the clip applier, the first rib is adjacent to the second body to retain the first boss in the second aperture, and the second rib is adjacent to the first body to retain the second boss in the first aperture.

According to yet another embodiment of the present invention, the first body comprises a first spring element contacting the second body, and the second body comprises a second spring element contacting the first body. The first and second spring elements bias the first and second jaws toward the open position.

According to still another embodiment of the present invention, the first body comprises a first rib extending toward the second body and the second body comprises a second rib extending toward the first body. The first rib is adjacent to the second rib at the open and closed positions of the clip applier to maintain alignment of the first jaw with the second jaw.

According to a further embodiment of the present invention, the first body comprises a first stop surface spaced from the first longitudinal wall, and the second body comprises a second stop surface spaced from the second longitudinal wall. At the closed position of the clip applier, the first and second stop surfaces abut each other to prevent further pivoting of the first and second jaws toward each other. Preferably, the abutment of the first and second stop surfaces maintains a gap between the first and second jaws to prevent the first and second jaws from contacting each other.

According to a yet further embodiment of the present invention, the first body comprises a first shoulder and a first protrusion transversely spaced from the first shoulder. The second body comprises a second shoulder and a second protrusion transversely spaced from the second shoulder at the open position of the clip applier. The first shoulder abuts against the second protrusion and the second shoulder abuts against the first protrusion to prevent further pivoting of the first and second jaws away from each other. Moreover, the first body can comprise a first recess defined between the first longitudinal wall and the first shoulder, and the second body can comprise a second recess defined between the second longitudinal wall and the second shoulder. During the pivoting of the first and second jaws between the open and closed positions, the first protrusion slides along the second recess and the second protrusion slides along the first recess.

According to an additional embodiment of the present invention, a fingertip-actuated surgical clip applier comprises a first body and a second body. The first body comprises a main section and a first jaw extending in a distal direction from the main section. The main section comprises a hinge region and a first longitudinal wall extending between the first jaw and the hinge region. The first longitudinal wall comprises a first outside surface adapted for contacting a first fingertip and an opposing first inside surface. The second body comprises a second main section and a second jaw extending in the distal direction from the second main section in opposing relation to the first jaw. The second main section comprises a second hinge region and a second longitudinal wall extending between the second jaw and the second hinge region. The second longitudinal wall comprises a second outside surface adapted for contacting a second fingertip, and a second inside surface generally facing the first inside surface. The second hinge region is pivotably connected to the first hinge region. The first and second jaws are pivotable toward each other to a closed position and away from each other to an open position.

According to another aspect of this embodiment, the main section comprises first and second lateral walls extending from the first longitudinal wall and transversely spaced from each other. The second main section comprises third and fourth lateral walls extending from the second longitudinal wall and transversely spaced from each other. The first lateral wall comprises a first boss, the second lateral wall comprises a first aperture, the third lateral wall comprises a second boss, and the fourth lateral wall comprises a second aperture. The first boss is pivotably disposed within the second aperture and the second boss is pivotably disposed within the first aperture.

According to yet another aspect of this embodiment, a first rib extends from the first inside surface of the first longitudinal wall, and a second rib extends from the second inside surface of the second longitudinal wall. The fourth lateral wall is interposed between the first rib and the first lateral wall to retain the first boss of the first lateral wall in the second aperture of the fourth lateral wall. The second lateral wall is interposed between the second rib and the third lateral wall to retain the second boss of the third lateral wall in the first aperture of the second lateral wall.

According to yet another aspect of this embodiment, the second lateral wall comprises a first spring element contacting the second inside surface of the second longitudinal wall. The fourth lateral wall comprises a second spring element contacting the first inside surface of the first longitudinal wall. The first and second spring elements bias the first and second jaws toward the open position of the clip applier.

According to still another aspect of this embodiment, at both the open and closed positions of the clip applier, the first lateral wall is adjacent to the fourth lateral wall and the second lateral wall is adjacent to the third lateral wall. This configuration maintains alignment of the first jaw with the second jaw.

The present invention also provides a method for manipulating a surgical clip comprising the following steps. A fingertip-actuated clip applier is provided that comprises a first body and a second body. The first body comprises a main section and a first jaw extending in a distal direction from the main section. The main section comprises a hinge region and a first longitudinal wall extending between the first jaw and the hinge region. The second body comprises a second jaw and a second longitudinal wall. The second body is inverted in relation to the first body, and is pivotably connected to the hinge region. The first and second jaws are pivotable toward each other to a closed position and away from each other to an open position. The clip is loaded into engagement with the first and second jaws. The clip applier is grasped by contacting the first longitudinal wall with a first fingertip and the second longitudinal wall with a second fingertip such that the first and second fingertips generally oppose each other. The first and second fingertips are moved toward each other to cause the first and second jaws to pivot from the open position toward the closed position, thereby compressing the clip. In one aspect of this method, the first and second fingertips are moved toward each other against first and second biasing forces. The first biasing force is created by a first spring element of the first body that contacts the second body. The second biasing force is created by a second spring element of the second body that contacts the first body. The method also encompasses permitting the first and second fingertips to move away from each other to cause the first and second jaws to pivot toward the open position under the influence of the first and second biasing forces.

The present invention further provides a method for fabricating a fingertip-actuated surgical clip applier according to the following steps. A first polymeric workpiece is provided. A first body is formed from the workpiece. The first body comprises a main section and first jaw extending in a distal direction from the main section. The main section comprises a hinge region and a longitudinal wall extending between the first jaw and the hinge region. A second polymeric workpiece is provided. A second body is formed from the second workpiece. The second body is substantially structurally identical to the first body and comprises a second jaw. The second body is inverted in relation to the first body. The second body is connected to the first body such that the first and second jaws are disposed in opposing relation, and are pivotable toward each other to a closed position and away from each other to an open position.

According to another aspect of this method, a first boss is formed on the first body and a first aperture is formed in the first body. A second boss is formed on the second body and a second aperture is formed in the second body. The first and second bodies are connected together by inserting the first boss into the second aperture and the second boss into the first aperture.

It is therefore an object of the present invention to provide a surgical clip applying instrument capable of being actuated by the fingertips of the user.

It is another object of the present invention to provide a fingertip-actuated clip applying instrument adapted for manipulating surgical clips of the polymeric, asymmetric design.

It is yet another object of the present invention to provide a surgical clip applying instrument having a simpler construction and design than has been heretofore available.

It is still another object of the present invention to provide a surgical clip applying instrument that can be assembled by snapping together two identical or substantially identical body pieces.

It is an additional object of the present invention to provide a surgical clip applying instrument that is much smaller in size as compared to instruments heretofore available, so as to enable access to surgical sites not heretofore possible and to facilitate and improve access to other kinds of surgical sites.

It is a further object of the present invention to provide a surgical clip applying instrument that affords the user enhanced control over manipulation of a surgical clip and improved tactile feedback as the clip is being manipulated and/or latched.

Some of the objects of the invention having been stated hereinabove, and which are addressed in whole or in part by the present invention, other objects will become evident as the description proceeds when taken in connection with the accompanying drawings as best described hereinbelow.

DETAILED DESCRIPTION OF THE INVENTION

Figure 1A:
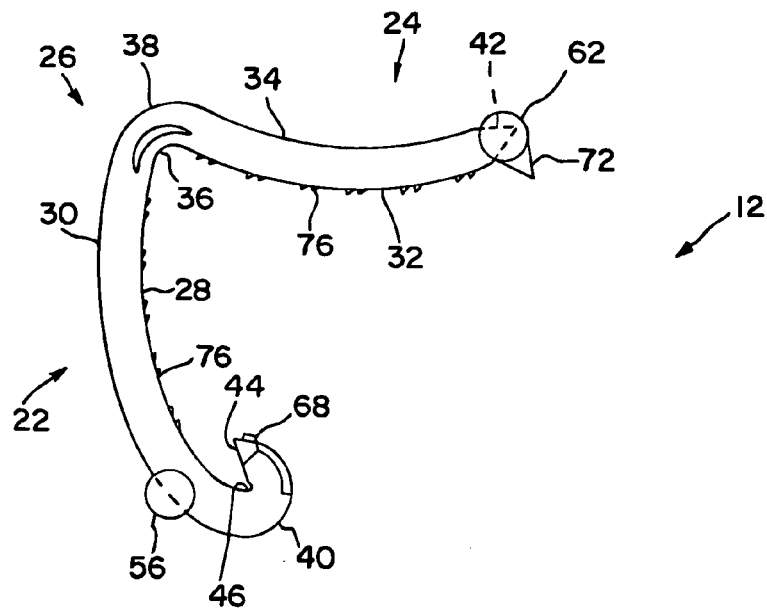
FIG. 1A is a side elevation view of one example of an asymmetric surgical clip suitable for use in conjunction with the clip applier of the present invention.
Figure 1B:
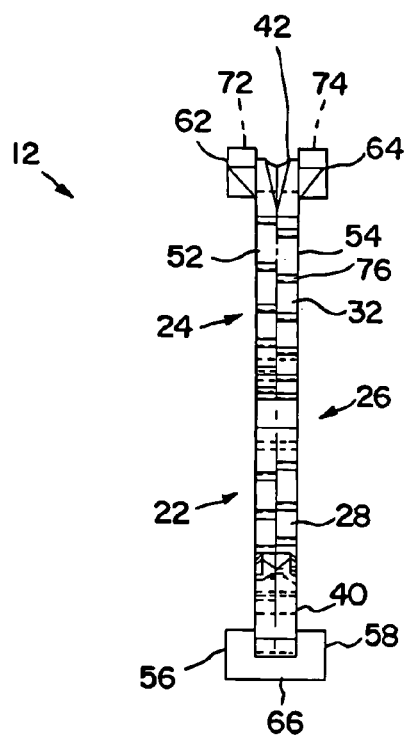
FIG. 1B is a front elevation view of the surgical clip illustrated in FIG. 1A directed into the open side of the clip.

The clip applier of the present invention as described in detail below is particularly designed for use in manipulating a polymeric, asymmetric clip that is movable into a closed, latched state when clamped onto tissue. An example of this type of clip, generally designated 12, is illustrated in FIGS. 1A and 1B. Clip 12 preferably comprises a one-piece integral polymeric body formed from a suitable strong, biocompatible engineering plastic such as the type commonly used for surgical implants. Examples include polyethylene terephthalate (PET), polybutylene terephthalate (PBT), polyoxymethylene, or other thermoplastic materials having similar properties that can be injection-molded, extruded or otherwise processed into like articles.

The body of clip 12 comprises a first or outer leg, generally designated 22, and a second or inner leg, generally designated 24. First and second legs 22 and 24 are joined at their proximal ends by an integral hinge or heel section, generally designated 26. First and second legs 22 and 24 have complementary arcuate profiles. Thus, first leg 22 has a concave inner surface 28 and a convex outer surface 30, and second leg 24 has a convex inner surface 32 and a concave outer surface 34. Convex inner surface 32 of second leg 24 and concave inner surface 28 of first leg 22 have substantially matching radii of curvature. Hinge section 26 has a continuous concave inner surface 36 and a continuous convex outer surface 38. Concave inner surface 36 of hinge section 26 joins concave inner surface 28 of first leg 22 and convex inner surface 32 of second leg 24. Convex outer surface 38 of hinge section 26 joins convex outer surface 30 of first leg 22 and concave outer surface 34 of second leg 24. First leg 22 transitions to a curved, C-shaped hook section 40 at its distal end. Second leg 24 transitions to a pointed tip section 42 at its distal end. Hook section 40 is distally reversely curved inwardly, and has a transverse beveled surface 44. Beveled surface 44 and concave inner surface 28 define a latching recess 46, which is adapted for conformally engaging tip section 42 in the course of compressing clip 12 into a latched or locked position around a vessel or other tissue.

As best shown in FIG. 1B, which is an elevation view directed into the open concave side of clip 12, clip 12 comprises parallel, opposed side surfaces 52 and 54. Typically, the body of clip 12 has a constant thickness between side surfaces 52 and 54. Adjacent to the distal end of the first leg 22 and immediately inwardly of hook section 40, a pair of cylindrical bosses 56 and 58 are formed coaxially on the opposed lateral surfaces of first leg 22. In the illustrated example of clip 12, a bridge section 66 couples bosses 56 and 58 together. As evident in FIG. 1A, bosses 56 and 58 project outwardly beyond convex outer surface 30 of first leg 22. Referring back to FIG. 1B, at the distal end of inner leg 24, another pair of cylindrical bosses 62 and 64 are formed coaxially on the opposed lateral surfaces of inner leg 24 at tip section 42. As evident in FIG. 1A, bosses 62 and 64 of second leg 24 extend longitudinally forwardly beyond tip section 42. Also in the illustrated example of clip 12, hook section 40 of first leg 22 terminates at a sharp tip 68, the distal end of second leg 24 includes a pair of sharp tissue-penetrating teeth 72 and 74, and both first and second legs 22 and 24 have a plurality of protrusions or teeth 76 extending from their respective inner surfaces 28 and 32. These latter features are designed to engage the tissue of the vessel being clamped and assist in preventing the vessel from sliding laterally or longitudinally during or following clip closure. It will be noted, however, that other clips equally suitable for use in conjunction with the invention do not contain such features.

In the practice of ligating a vessel as understood by persons skilled in the art, clip 12 is designed to be compressed into a latched or locked position around the vessel through the use of an appropriate clip applicator instrument, such as the known type described in the aforementioned U.S. Pat. No. 5,100,416, or the novel fingertip-actuated clip applying instrument described and claimed herein. The clip applicator instrument engages bosses 56, 58, 62 and 64 of clip 12 and pivots bosses 56, 58, 62 and 64 inwardly about hinge section 26. This causes first and second legs 22 and 24 to close around the vessel, with convex inner surface 32 of second leg 24 and complementary concave inner surface 28 of first leg 22 contacting the outer wall of the vessel. Tip section 42 of second leg 24 then begins to contact hook section 40.

Further pivotal movement by the applicator instrument 100 longitudinally elongates first leg 22 and deflects hook section 40, allowing tip section 42 to align with latching recess 46. Upon release of the applicator instrument 100, tip section 42 snaps into and is conformally seated in latching recess 46, at which point clip 12 is in its latched condition. In the latched condition, tip section 42 is engaged between concave inner surface 28 and beveled surface 44, thereby securely clamping a designated vessel or other tissue between concave inner surface 28 and convex inner surface 32.

Clips similar to clip 12 are described in detail in commonly assigned U.S. Pat. No. 4,834,096 to Oh et al. and U.S. Pat. No. 5,062,846 to Oh et al., the disclosures of which are incorporated herein in their entireties. In addition, a particularly suitable clip is the HEM-O-LOK® clip commercially available from the assignee of the present invention. These clips are currently available in sizes designated "M", "ML", and "L". The clip applier of the invention described hereinbelow can be dimensioned to specifically handle any sizes of HEM-O-LOK® clips commercially available.

Figure 2:
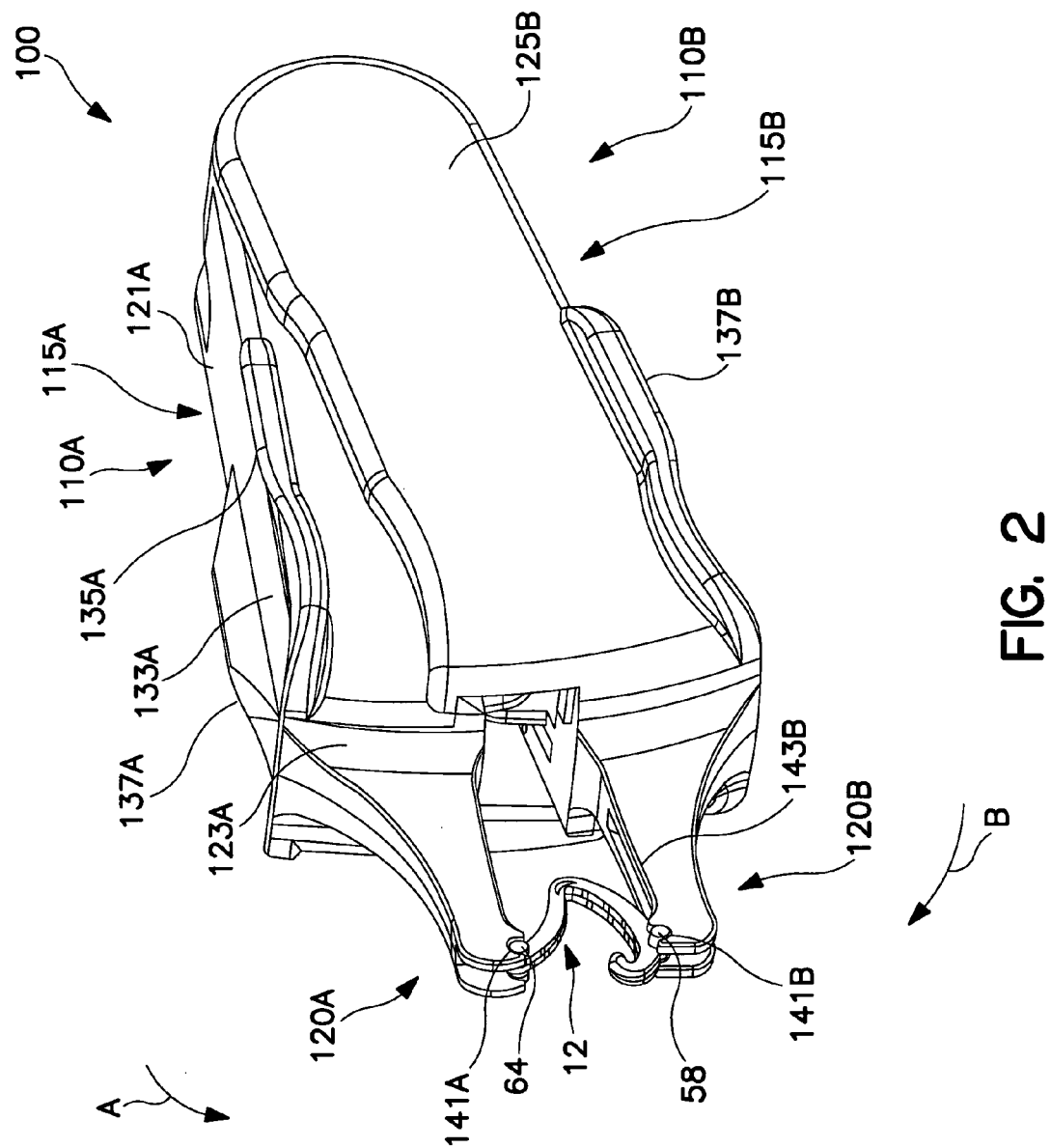
FIG. 2 is a perspective view of a clip applier of the present invention shown in an open position with a surgical clip loaded in its jaws.
Figure 3:
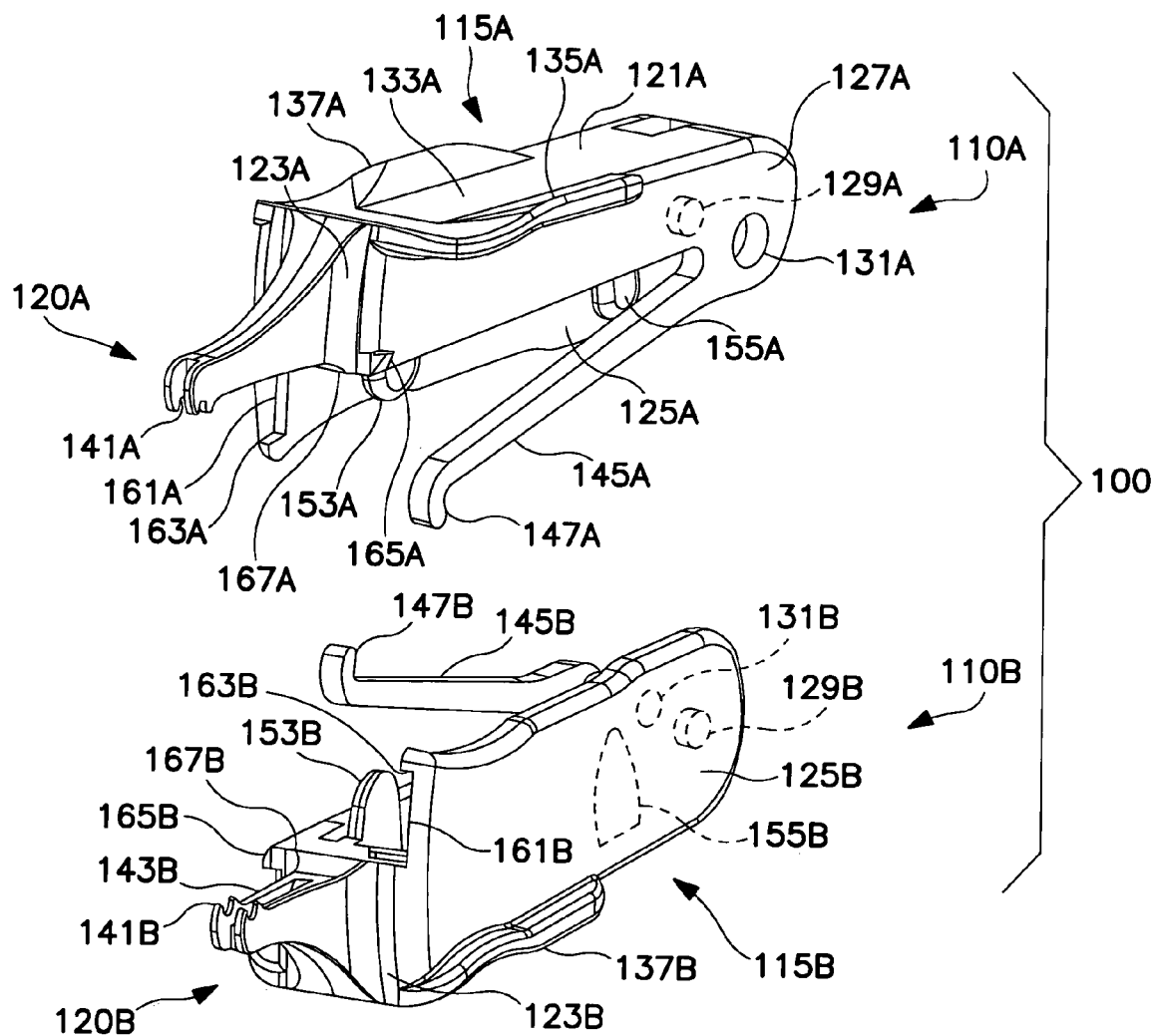
FIG. 3 is a perspective view showing the two unassembled structural halves of the clip applier illustrated in FIG. 2.

Referring now to FIGS. 2 and 3, a fingertip-actuated clip applier, according to the present invention, generally designated 100, is illustrated in assembled and unassembled configurations, respectively, in accordance with an exemplary, preferred embodiment of the present invention. In the preferred embodiment, as particularly shown in FIG. 3, clip applier 100 generally comprises two identical structural halves: a first clip applier body generally designated 110A, and a second clip applier body generally designated 110B. Preferably, first and second bodies 110A and 110B each are constructed as unitary components from a suitable biocompatible material such as a molded plastic, e.g., nylon, polycarbonate, ABS (acrylonitrile butadiene styrene) or any of these materials that have been reinforced with glass or carbon fibers. The various features of clip applier 100 described below are formed from the unitary structures of first and second bodies 110A and 110B. In one example, first and second bodies 110A and 110B are each 2 inches in length from their respective proximal ends to their distal jaw-containing ends. By comparison, the overall length of a conventional clip applier typically ranges from about 8–11 inches.

Referring to FIG. 3, first body 110A comprises a first main section, generally designated 115A, and a first jaw, generally designated 120A. First main section 115A comprises a first longitudinal wall 121A, a first distal end wall 123A from which first jaw 120A extends outwardly in the distal direction, a first boss-side lateral wall 125A, and a first aperture-side lateral wall 127A. First distal end wall 123A, first boss-side lateral wall 125A, and first aperture-side lateral wall 127A extend from first longitudinal wall 121A, thereby cooperatively defining a partially enclosed chamber associated with first main section 115A. A first pivot boss 129A extends transversely into the chamber of first body 110A from an inside surface of first boss-side lateral wall 125A. A first aperture 131A is formed in first aperture-side lateral wall 127A and is disposed generally across the chamber from first pivot boss 129A.

As indicated above, second body 110B is preferably structurally identical to first body 110A, and thus likewise comprises a second main section generally designated 115B, and a second jaw generally designated 120B. Second main section 115B comprises a second longitudinal wall 121B (see FIG. 8), a second distal end wall 123B from which second jaw 120B extends outwardly in the distal direction, a second boss-side lateral wall 125B, and a second aperture-side lateral wall 127B (see FIG. 8). Second distal end wall 123B, second boss-side lateral wall 125B, and second aperture-side lateral wall 127B extend from second longitudinal wall 121B, thereby cooperatively defining a partially enclosed chamber associated with second main section 115B. A second pivot boss 129B extends transversely into the chamber of second body 110B from an inside surface of second boss-side lateral wall 125B. A second aperture 131B is formed in second aperture-side lateral wall 127B and is disposed generally across the chamber from second pivot boss 129B.

Clip applier 100 is assembled by inverting second body 110B with respect to first body 110A as shown in FIG. 3, and securing first and second bodies 110A and 110B together at their respective rear or proximal ends. As shown in the rear view of FIG. 8, this is accomplished by inserting first pivot boss 129A into second aperture 131B and second pivot boss 129B into first aperture 131A. When first and second bodies 110A and 110B are assembled together in this manner, first and second jaws 120A and 120B oppose each other as shown in FIG. 2. The connection made between first and second bodies 110A and 110B at their proximal ends enables first and second bodies 110A and 110B to pivot with respect to each other. As a result, first and second jaws 120A and 120B are likewise pivotable with respect to each other, and thus are movable toward and away from each other between open and closed positions, respectively, as indicated by arrows A and B in FIG. 2. As also shown in FIG. 2, this movement enables the user of clip applier 100 to manipulate a tissue-ligating clip, such as clip 12 described in detail above and illustrated in FIGS. 1A and 1B, in the course of an appropriate surgical procedure.

Figure 6:
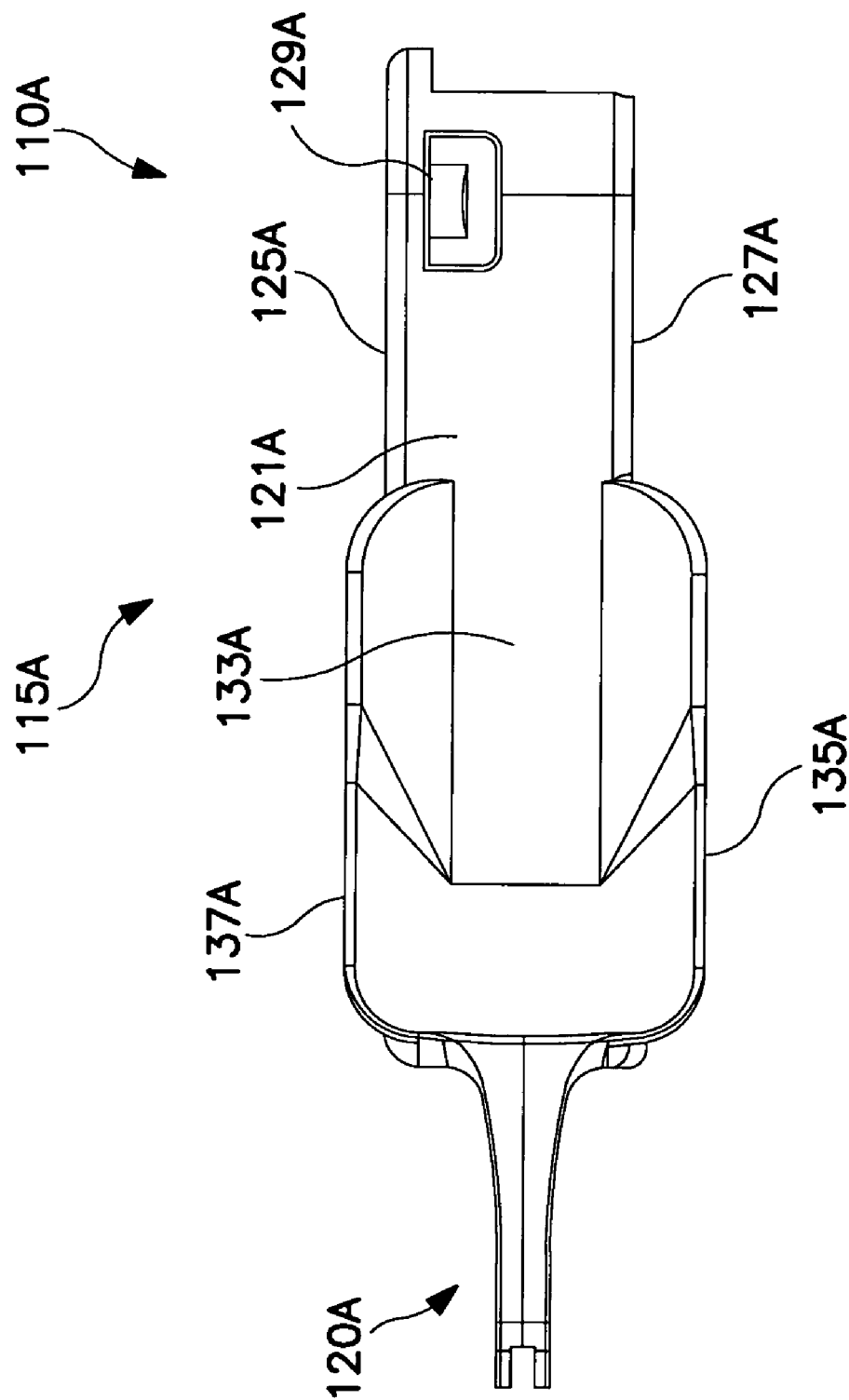
FIG. 6 is a top plan view of the clip applier half showing outside features thereof.

It will be noted that conventional clip appliers contain some form of a handle or grip assembly remotely disposed from their jaws through a distance (e.g., eleven inches) dictated by an elongate shaft section (or a pair of scissors-like arms) interposed between the jaws and the handles. By contrast, clip applier 100 of the present invention is designed to be manipulated by an opposing pair of fingertips (e.g., the tips of the thumb and index finger) of the user. In this manner, the user can actuate first and second jaws 120A and 120B to compress clip 12 into its latched state by squeezing clip applier 100 between the user's fingertips. This fingertip-actuated manipulation of clip 12 is facilitated by providing first and second longitudinal walls 121A and 121B of first and second bodies 110A and 110B with respective first and second fingertip areas 133A and 133B, as shown in FIGS. 2, 3, 6 and 8. First and second fingertip areas 133A and 133B (FIG. 8) are contoured to respectively include opposing winged sections 135A/137A and 135B/137B (FIG. 8) on both sides of the longitudinal axis of clip applier 100. As used herein, the term "contoured" is broadly taken to mean non-planar. In addition, as best shown in FIG. 6 (specifically illustrating first body 110A but analogous to second body 110B), first and second fingertip areas 133A and 133B are preferably wider than the remaining portions of first and second longitudinal walls 121A and 121B. In one example, first and second fingertip areas 133A and 133B, including winged sections 135A, 137A, 135B and 137B, are each 9/16 inch in width. These features improve contact between clip applier 100 and the fingertips of the user, as well as control over clip applier 100 by the user and, consequently, control over manipulation of clip 12.

In FIG. 2, clip 12 is securely loaded into first and second jaws 120A and 120B. For this purpose, as best shown in FIG. 3, first jaw 120A has a pair of first jaw recesses 141A at its distal end and second jaw 120B has a pair of second jaw recesses 141B at its distal end. First jaw recesses 141A securely engage a pair of bosses 56/58 or 62/64 of clip 12 and second jaw recesses 141B securely engage the opposite pair of bosses 62/64 or 56/58. It will be noted that in the perspective view of FIG. 2, only bosses 58 and 64 of clip 12 are shown. First jaw 120A also includes a first open jaw channel 143A (see FIG. 5) and second jaw 120B includes a second open jaw channel 143B (see FIGS. 2 and 3). First and second jaw channels 143A and 143B accommodate legs 22 and 24 of clip 12 (see FIG. 1A) to enhance control over clip 12 and securement of clip 12 in first and second jaws 120A and 120B.

Figure 4:
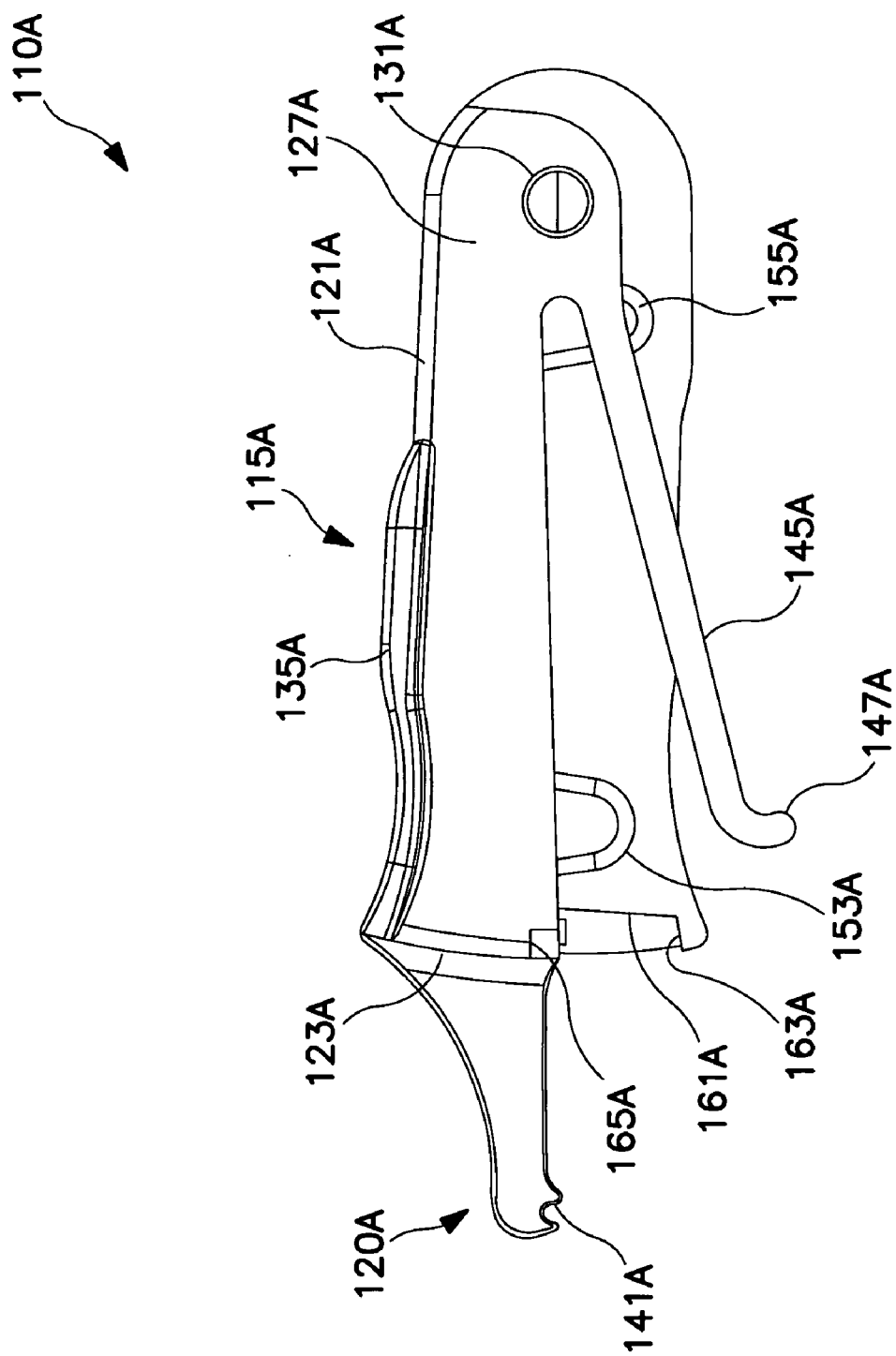
FIG. 4 is a side elevation view of one of the clip applier halves.
Figure 5:
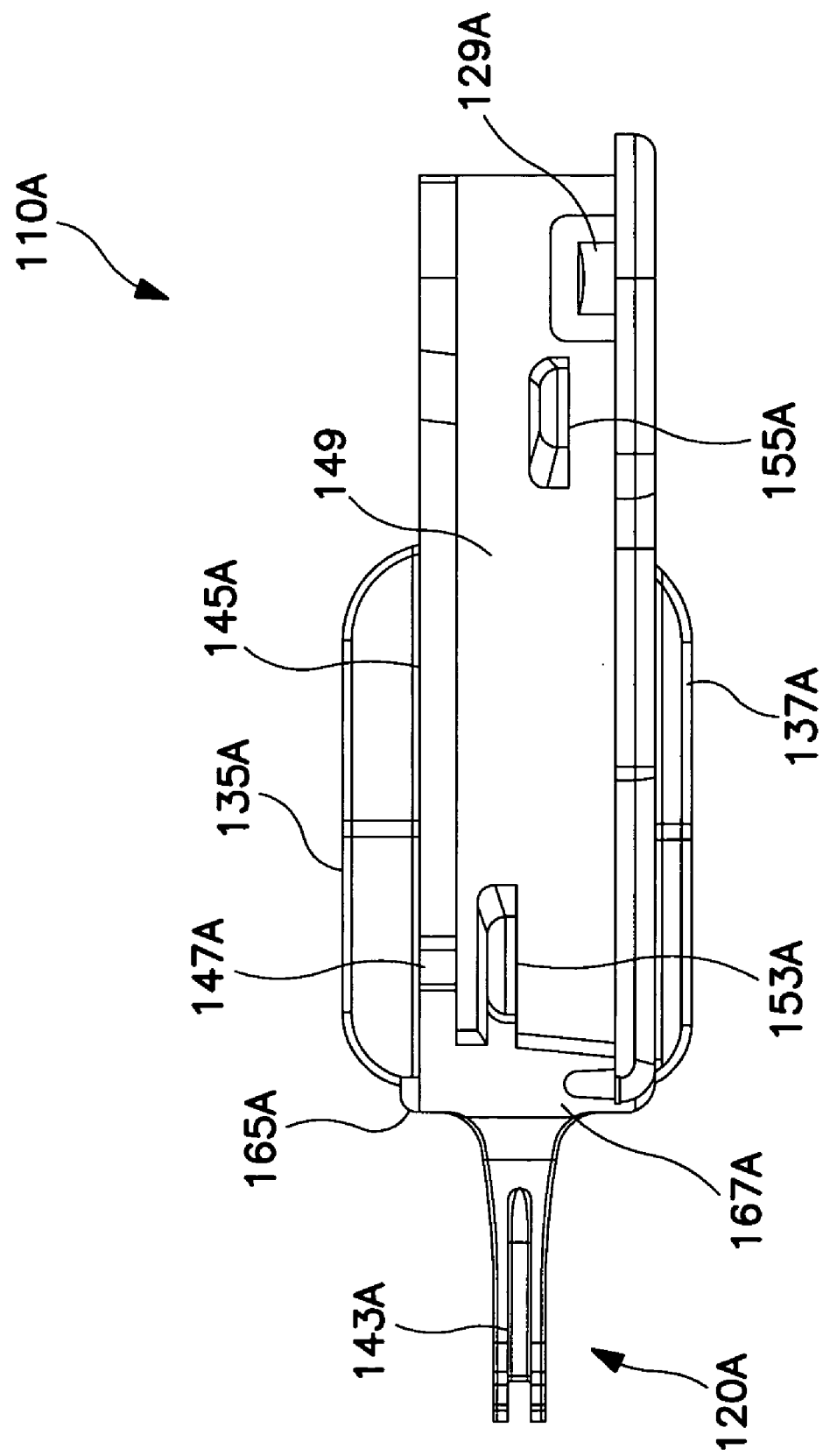
FIG. 5 is a bottom plan view of the clip applier half of FIG. 4, showing inside features thereof.

Additional features of clip applier 100 will now be described with reference primarily to FIGS. 3–8. It will be understood that while the features illustrated in FIGS. 4–6 are described only in relation to first body 110A of clip applier 100, FIGS. 4–6 are equally representative of second body 110B. That is, second body 110B is identical or substantially identical to first body 110A and hence includes a corresponding set of the same features as first body 110A.

Referring now to FIG. 4, first body 110A comprises a first spring element 145A extending at an angle from the proximal region of first aperture-side lateral wall 127A toward the distal end of first body 110A. First spring element 145A terminates at a first arcuate contact region 147A. As shown in FIG. 3, second body 110B comprises a similar second spring element 145B with a second arcuate contact region 147B. The dimensions of first and second spring elements 145A and 145B and the material selected for first and second bodies 110A and 110B are sufficient to render first and second spring elements 145A and 145B resilient and deflectable, and hence capable of storing spring energy. In the assembled, operational form of clip applier 100, first arcuate contact region 147A of first spring element 145A bears against an inside surface (not shown) of second longitudinal wall 121B (see FIGS. 2 and 3) of second body 110B, and second spring element 145B bears against an inside surface 149 (see FIG. 5) of first longitudinal wall 121A of first body 110A. By this configuration, first and second spring elements 145A and 145B bias clip applier 100 toward its open position when the fingertips of the user are not imparting sufficient force to first and second fingertip areas 133A and 133B of first and second longitudinal walls 121A and 121B.

Referring now to FIGS. 3 and 5, first body 110A further comprises a first distal rib 153A and a first proximal rib 155A disposed in its chamber, both of which depend from inside surface 149 (FIG. 5) of first longitudinal wall 121A. Second body 110B also comprises a second distal rib 153B and a second proximal rib 155B disposed in its chamber, which depend from the inside surface (not shown) of second longitudinal wall 121B. As shown in the front view of clip applier 100 in FIG. 7A and the rear view in FIG. 8, first distal rib 153A and first proximal rib 155B are offset from each other relative to the central vertical axis of clip applier 100, and second distal rib 153B and second proximal rib 155B are likewise offset from each other in relation to the same reference axis. In the assembled form of clip applier 100 shown in FIG. 7A, first and second distal ribs 153A and 153B are disposed adjacent to each other. A juxtaposition is thus created between first and second distal ribs 153A and 153B, as well as between first boss-side lateral wall 125A and second aperture-side lateral wall 127B, and between second boss-side lateral wall 125B and first aperture-side lateral wall 127A. These juxtapositions restrict lateral movement of first and second bodies 110A and 110B with respect to each other, and thus assist in maintaining proper alignment of first and second jaws 120A and 120B with respect to each other.

Figure 8:
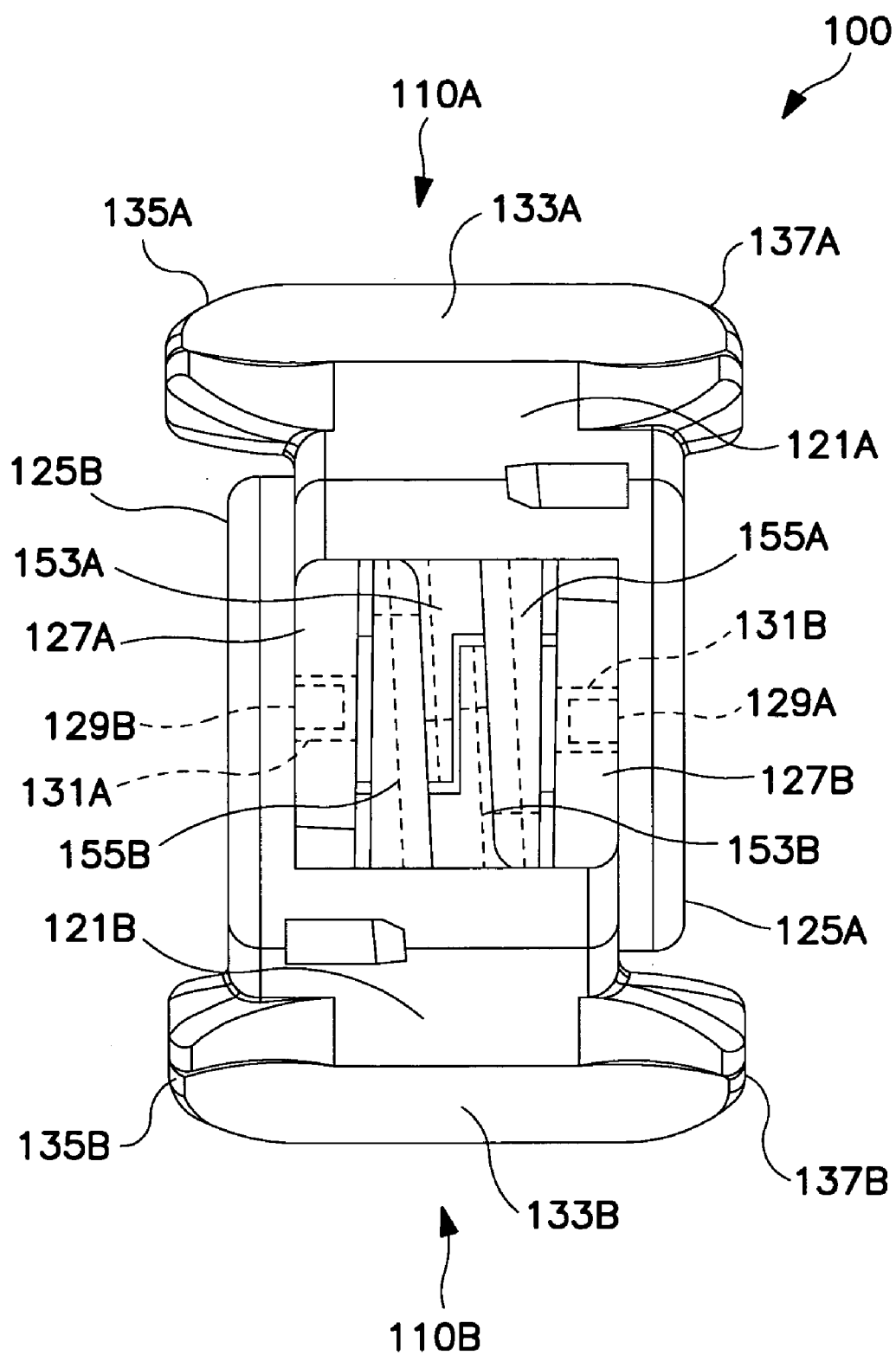
FIG. 8 is a rear elevation of the clip applier.

As shown in FIG. 8, first proximal rib 155A is disposed adjacent to second aperture-side lateral wall 127B and second proximal rib 155B is disposed adjacent to first aperture-side lateral wall 127A. These juxtapositions also restrict lateral movement of first and second bodies 110A and 110B with respect to each other. Moreover, the location of first proximal rib 155A within the interior of clip applier 100 assists in maintaining second aperture-side lateral wall 127B in close proximity to first boss-side lateral wall 125A, and thus assists in retaining first pivot boss 129A in second aperture 131B. Likewise, the location of second proximal rib 155B within the interior of clip applier 100 assists in maintaining first aperture-side lateral wall 127A in close proximity to second boss-side lateral wall 125B, and thus assists in retaining second pivot boss 129B in first aperture 131A.

Figure 7A:
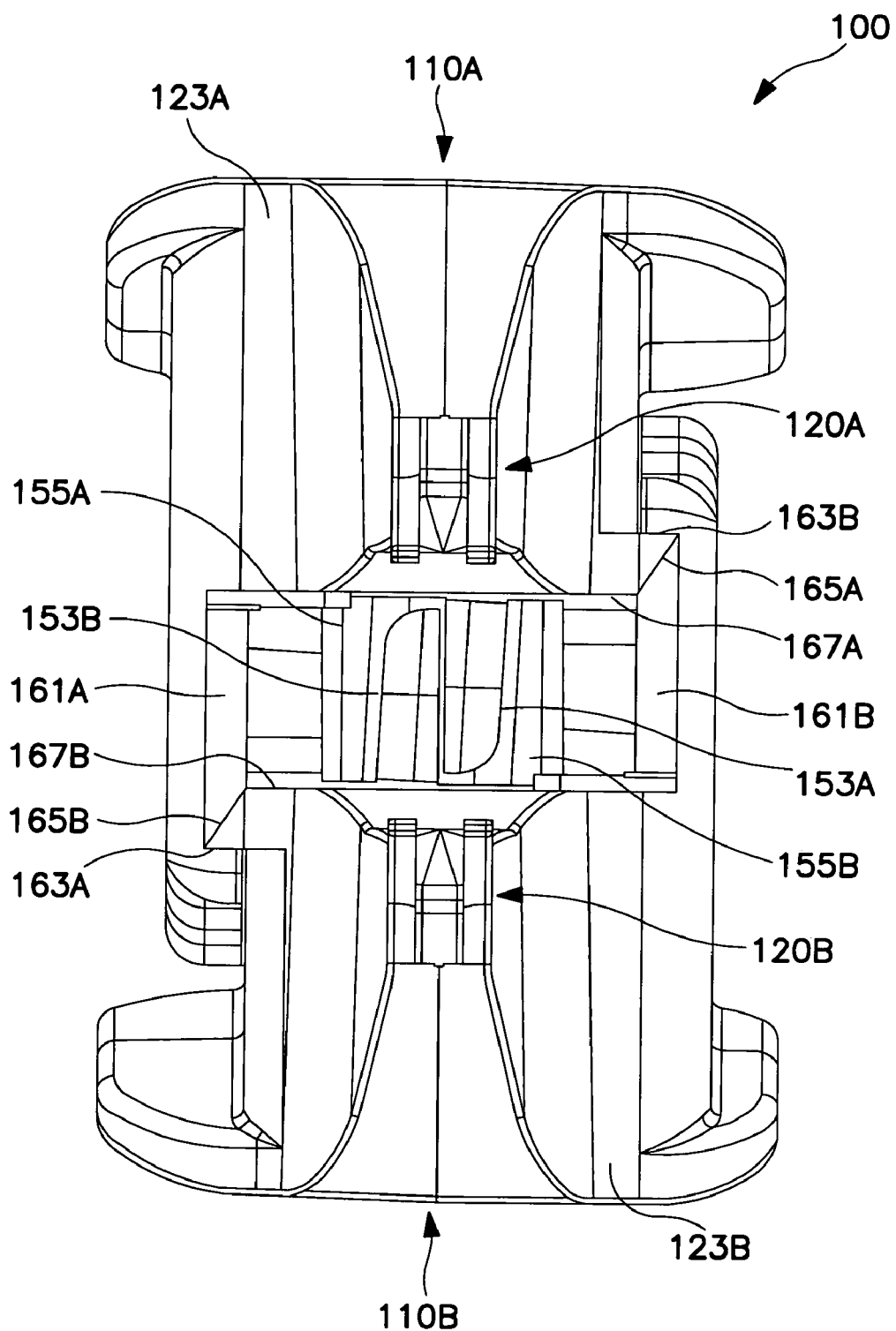
FIG. 7A is a front elevation view of the clip applier in its open position.
Figure 7B:
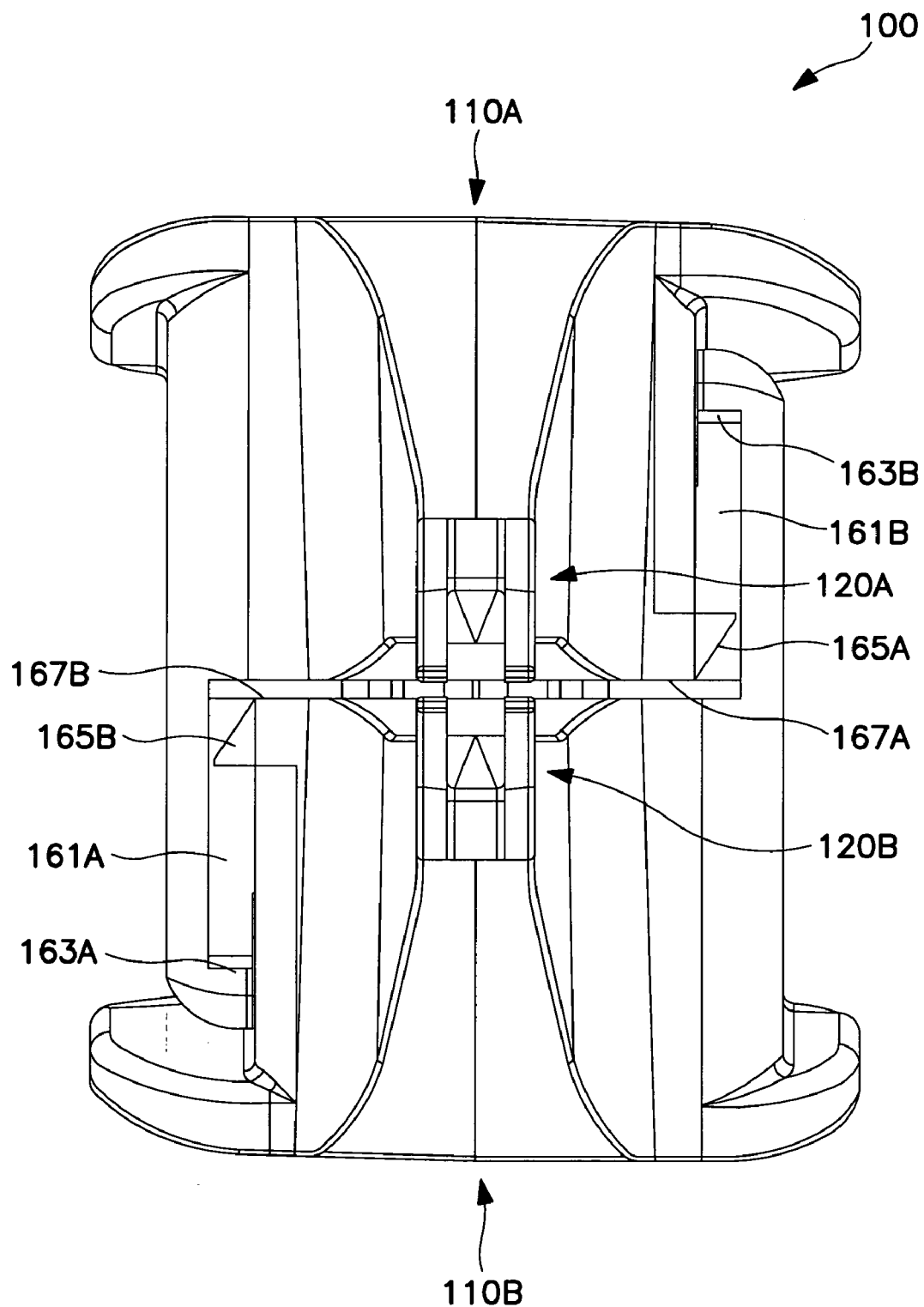
FIG. 7B is a front elevation view of the clip applier in its closed position.

Referring now to the front elevation views of FIGS. 7A and 7B, clip applier 100 is movable between an extreme open position (FIG. 7A) and an extreme closed position (FIG. 7B). Both first and second bodies 110A and 110B of clip applier 100 include an identical set of features that cooperatively define the extreme open position of clip applier 100, and thus limit the degree to which first and second jaws 120A and 120B can open. First body 110A includes a first recess or track 161A formed in the edge of first boss-side lateral wall 125A. First track 161A extends from first distal end wall 123A and terminates at a first open-position stop surface 163A. A first stop element 165A protrudes transversely outwardly from first aperture-side lateral wall 127A. Analogously, second body 110B includes a second recess or track 161B formed in the edge of second boss-side lateral wall 125B. Second track 161B extends upwardly from second distal end wall 123B and terminates at a second open-position stop surface 163B. A second stop element 165B protrudes transversely outwardly from second aperture-side lateral wall 127B. It is evident from FIGS. 7A and 7B that, as first and second jaws 120A and 120B pivot away from each other under the influence of first and second spring elements 145A and 145B (see FIG. 3), first stop element 165A travels along the length of second track 161B and second stop element 165B travels along the length of first track 161A. As shown in FIG. 7A, first stop element 165A eventually abuts against second open position stop surface 163B and second stop element 165B eventually abuts against first open position stop surface 163A. Further opening movement of first and second jaws 120A and 120B is prevented. These features enable enhanced control over clip 12 by the user by ensuring that clip 12 remains properly aligned and loaded in first and second jaws 120A and 120B, with bosses 56, 58, 62 and 64 of clip 12 (see FIGS. 1A–2) secured in first and second jaw recesses 141A and 141B and first and second legs 22 and 24 of clip 12 retained in first and second jaw channels 143A and 143B.

Figure 9:
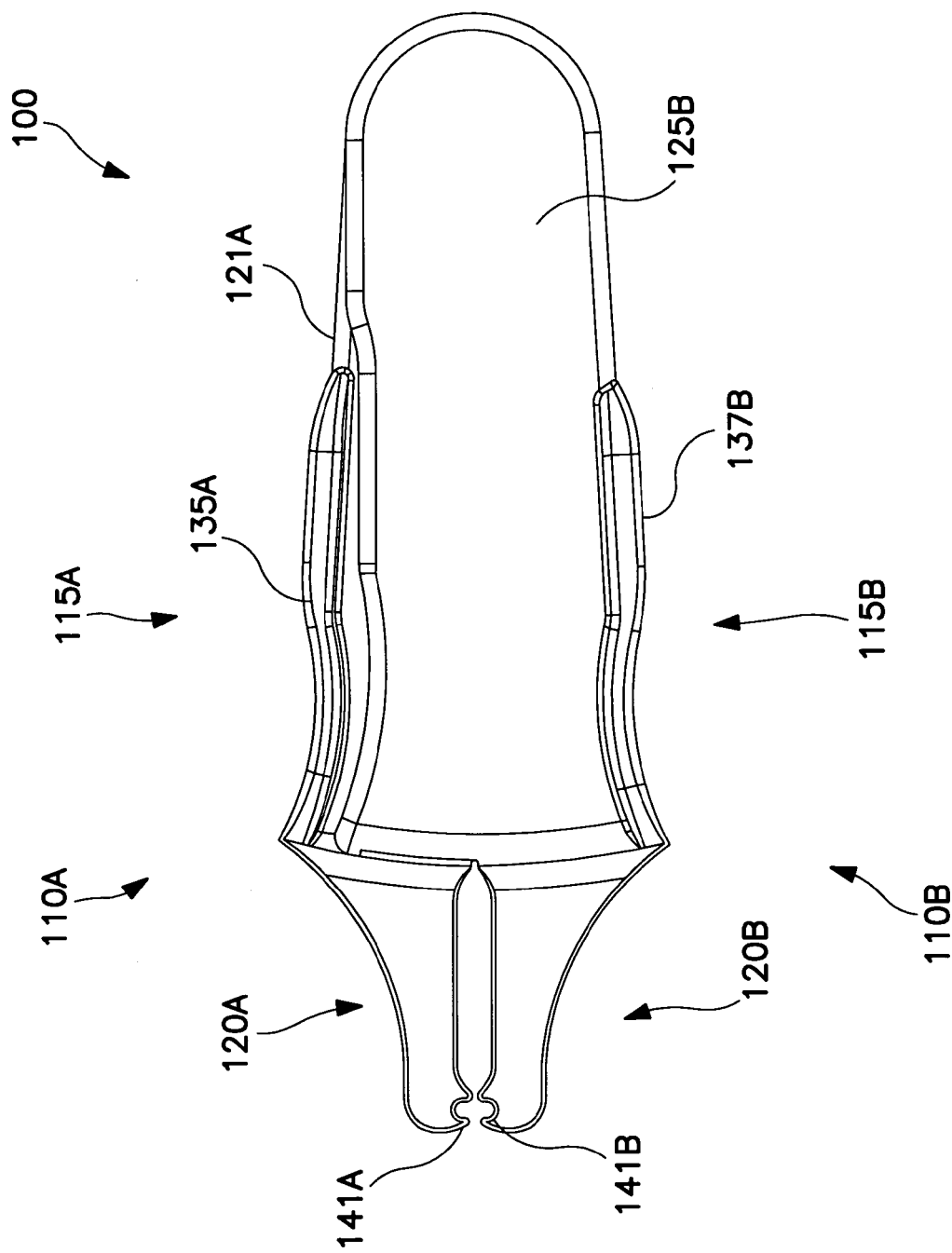
FIG. 9 is a side elevation view of the clip applier in its closed position.

First and second bodies 110A and 110B of clip applier 100 also include first and second opposing closed-position stop surfaces 167A and 167B that cooperatively define the extreme closed position of clip applier 100, and thus limit the degree to which first and second jaws 120A and 120B can close. Preferably, first closed-position stop surface 167A is the edge of first distal end wall 123A opposite first longitudinal wall 121A, and second closed-position stop surface 167B is the edge of second distal end wall 123B opposite second longitudinal wall 121B. For clarity, a gap is illustrated in FIG. 7B between first and second closed-position stop surfaces 167A and 167B. It will be evident from FIG. 7B, however, that the abutment of first and second closed-position stop surfaces 167A and 167B against each other upon actuation of clip applier 100 maintains a small gap between first and second jaws 120A and 120B. The gap between first and second jaws 120A and 120B is best shown in FIG. 9. This feature lowers the risk of pinching or damaging tissue at a surgical site during use of clip applier 100.

In accordance with the invention, clip applier 100 can be used to manipulate clip 12 in much the same manner as conventional clip appliers. Clip 12 is first loaded into first and second jaws 120A and 120B of clip applier 100, such as by the known method of inserting clip applier 100 into a clip cartridge, a desired surgical site is accessed by a known procedure, and clip applier 100 is actuated by the surgeon to apply clip 12 to a target vessel or other tissue. An example of a typical application of clip 12 to a vessel is given hereinabove. As noted above, however, only the fingertips of the surgeon are needed to handle and actuate clip applier 100. The design of clip applier 100 enables to surgeon to easily maneuver clip applier 100 around the surgical site, and make quick decisions and adjustments regarding where to actually apply 12 to completion. The invention is not limited to the types of surgical procedures in which clip applier 100 can be implemented. Any open surgery requiring the use of surgical clips is contemplated. In addition, clip applier 100 could be employed with the HALS procedure discussed hereinabove. It is contemplated that clip applier 100 could be inserted through the port created by the above-described inflatable device to access the abdominal cavity, thereby eliminating the need for an endoscopic clip applier. In addition to general ligating procedures and HALS procedures, other examples of surgical procedures for which clip applier 100 can be employed include vasectomies, lymph node dissections, and tubal ligations.

It will be understood that various details of the invention may be changed without departing from the scope of the invention. Furthermore, the foregoing description is for the purpose of illustration only, and not for the purpose of limitation—the invention being defined by the claims.

What is claimed is:

1. A fingertip-actuated surgical clip applier comprising:
    (a) a first body comprising a main section and a first jaw extending in a distal direction from the main section, the main section comprising a hinge region and a first longitudinal wall extending between the first jaw and the hinge region, the first longitudinal wall comprising a first outside surface adapted for contacting a first fingertip; and
    (b) a second body substantially structurally identical to the first body and comprising a second jaw and a second longitudinal wall, the second longitudinal wall comprising a second outside surface adapted for contacting a second fingertip, the second body inverted in relation to the first body and pivotably connected to the hinge region, wherein the first and second jaws are pivotable toward each other to a closed position and away from each other to an open position and wherein the first body comprises a first boss and a first aperture, the second body comprises a second boss and a second aperture, the first boss is pivotably disposed within the second aperture, and the second boss is pivotably disposed within the first aperture.

2. The clip applier according to claim 1 comprising a first rib extending from the first body toward the second body and a second rib extending from the second body toward the first body wherein, at both the open and closed positions, the first rib is adjacent to the second body to retain the first boss in the second aperture, and the second rib is adjacent to the first body to retain the second boss in the first aperture.

3. A fingertip-actuated surgical clip applier comprising:
    (a) a first body comprising a main section and a first jaw extending in a distal direction from the main section, the main section comprising a hinge region and a first longitudinal wall extending between the first jaw and the hinge region, the first longitudinal wall comprising a first outside surface adapted for contacting a first fingertip; and
    (b) a second body substantially structurally identical to the first body and comprising a second jaw and a second longitudinal wall, the second longitudinal wall comprising a second outside surface adapted for contacting a second fingertip, the second body inverted in relation to the first body and pivotably connected to the hinge region, wherein the first and second jaws are pivotable toward each other to a closed position and away from each other to an open position and wherein the first body comprises a first shoulder and a first protrusion transversely spaced from the first shoulder, the second body comprises a second shoulder and a second protrusion transversely spaced from the second shoulder and, at the open position, the first shoulder abuts against the second protrusion and the second shoulder abuts against the first protrusion to prevent further pivoting of the first and second jaws away from each other.

4. The clip applier according to claim 3 wherein the first body comprises a first recess defined between the first longitudinal wall and the first shoulder, the second body comprises a second recess defined between the second longitudinal wall and the second shoulder and, during pivoting of the first and second jaws between the open and closed positions, the first protrusion slides along the second recess and the second protrusion slides along the first recess.

5. A fingertip-actuated surgical clip applier comprising:
    (a) a first body comprising a first main section and a first jaw extending in a distal direction from the first main section, the first main section comprising a first hinge region and a first longitudinal wall extending between the first jaw and the first hinge region, the first longitudinal wall comprising a first outside surface adapted for contacting a first fingertip and an opposing first inside surface, wherein the first body comprises a first shoulder and a first protrusion transversely spaced from the first shoulder; and
    (b) a second body comprising a second main section and a second jaw extending in the distal direction from the second main section in opposing relation to the first jaw, the second main section comprising a second hinge region and a second longitudinal wall extending between the second jaw and the second hinge region, the second longitudinal wall comprising a second outside surface adapted for contacting a second fingertip and a second inside surface generally facing the first inside surface, wherein the second hinge region is pivotably connected to the first hinge region, and the first and second jaws are pivotable toward each other to a closed position and away from each other to an open position and wherein the first body comprises a first stop surface spaced from the first longitudinal wall, the second body comprises a second stop surface spaced from the second longitudinal wall and, at the closed position, the first and second stop surfaces abut each other to prevent further pivoting of the first and second jaws toward each other, wherein the second body comprises a second shoulder and a second protrusion transversely spaced from the second shoulder and, at the open position, the first shoulder abuts against the second protrusion and the second shoulder abuts against the first protrusion to prevent further pivoting of the first and second jaws away from each other.

6. The clip applier according to claim 5 wherein the abutment of the first and second stop surfaces maintains a gap between the first and second jaws to prevent the first and second jaws from contacting each other.

7. A fingertip-actuated surgical clip applier comprising:
    (a) a first body comprising a first main section and a first jaw extending in a distal direction from the first main section, the first main section comprising a first hinge region and a first longitudinal wall extending between the first jaw and the first hinge region, the first longitudinal wall comprising a first outside surface adapted for contacting a first fingertip and an opposing first inside surface; and
    (b) a second body comprising a second main section and a second jaw extending in the distal direction from the second main section in opposing relation to the first jaw, the second main section comprising a second hinge region and a second longitudinal wall extending between the second jaw and the second hinge region, the second longitudinal wall comprising a second outside surface adapted for contacting a second fingertip and a second inside surface generally facing the first inside surface, wherein the second hinge region is pivotably connected to the first hinge region, and the first and second jaws are pivotable toward each other to a closed position and away from each other to an open position and wherein the first body comprises a first shoulder and a first protrusion transversely spaced from the first shoulder, the second body comprises a second shoulder and a second protrusion transversely spaced from the second shoulder and, at the open position, the first shoulder abuts against the second protrusion and the second shoulder abuts against the first protrusion to prevent further pivoting of the first and second jaws away from each other.

8. The clip applier according to claim 7 wherein the first body comprises a first recess defined between the first longitudinal wall and the first shoulder, the second body comprises a second recess defined between the second longitudinal wall and the second shoulder and, during pivoting of the first and second jaw between the open and closed positions, the first protrusion slides along the second recess and the second protrusion slides along the first recess.

* * * * *